(12) United States Patent
Sheu et al.

(10) Patent No.: US 8,772,329 B2
(45) Date of Patent: Jul. 8, 2014

(54) **COMPOUNDS FROM MYCELIUM OF *ANTRODIA CINNAMOMEA* AND USE THEREOF**

(75) Inventors: Chia-Chin Sheu, Taoyuan County (TW); Masao Hattori, Toyama (JP)

(73) Assignee: Simpson Biotech Co., Ltd., Taoyuan County (TW)

( * ) Notice: Subject to any disclaimer, the term of this patent is extended or adjusted under 35 U.S.C. 154(b) by 632 days.

(21) Appl. No.: 12/811,115

(22) PCT Filed: Jan. 28, 2008

(86) PCT No.: PCT/CN2008/000196
§ 371 (c)(1),
(2), (4) Date: Jun. 29, 2010

(87) PCT Pub. No.: WO2009/094807
PCT Pub. Date: Aug. 6, 2009

(65) Prior Publication Data
US 2010/0286227 A1  Nov. 11, 2010

(51) Int. Cl.
*C07C 235/34* (2006.01)
*C07D 207/444* (2006.01)
*C07D 307/60* (2006.01)
*A61K 31/366* (2006.01)
*C07D 207/46* (2006.01)
*C07D 207/50* (2006.01)

(52) U.S. Cl.
CPC ............ *C07C 235/34* (2013.01); *C07D 207/46* (2013.01); *C07D 207/50* (2013.01); *C07D 307/60* (2013.01); *C07D 207/444* (2013.01)
USPC ........... 514/423; 514/425; 514/473; 514/553; 514/563; 514/570; 548/534; 548/542; 548/548; 549/253; 560/55; 562/444; 562/465

(58) Field of Classification Search
None
See application file for complete search history.

(56) References Cited

PUBLICATIONS

HCV—infection, http://www.caps.ucsf.edu/pubs/FS/revhepC.php (2010).*
Chang et al., Journal of Food and Drug Analysis, vol. 14, 2006, 174-182.*
Weber et al., American Laboratory, 2007, 39, 9-11.*
Caffein, "Caffeine Experiment".*
Caffein—dated, 1999, http://web.archive.org/web/19991004145709/http://www.umsl.edu/~orglab/pdffiles/caffein.pdf.*
Lu et al., Life Sciences 79, 2006, 252-258.*
Yaya Liu et al., Hepatitis C NS3 Protease Inhibition by Peptidyl-a-Ketoamide Inhibitors: Kinetic Mechanism and Structure, Archives of Biochemistry and Biophysics, 2004, pp. 207-216, vol. 421.
Nobuko Kakiuchi et al., A High Throughput Assay of the Hepatitis C Virus Nonstructural Protein 3 Serine Proteinase, Journal of Virological Methods, 1999, pp. 77-84, vol. 80.
I-Hwa Cherng et al., Three New Triterpenoids from *Antrodia cinnamomea*, Journal of Natural Products, Mar. 1995, pp. 365-371, vol. 58, No. 3.
Norio Nakamura et al., Five New Maleic and Succinic Acid Derivatives from the Mycelium of *Antrodia camphorata* and Their Cytotoxic Effects on LLC Tumor Cell Line, Journal of Natural Products, 2004, pp. 46-48, vol. 67.
Akiba T et al., Clinical Study of Shoshi on Japanese Hepatitis Patients Infected with C Type Hepatitis Virus, The Second Taiwan and Japan Symposium on *Antrodia cinnamomea*, Abst., 2007, pp. 82-98.
En-Shyh Lin et al., Factors Affecting Mycelial Biomassand Exopolysaccharide Production in Submerged Culvitation of *Antrodia cinnamomea* Using Complex Media, Bioresource Technology, 2007, pp. 2511-2517, vol. 98.
Hao-Feng Han et al., Protective Effects of a Neutral Polysaccharide Isolated from the Mycelium of *Antrodia cinnamomea* on Propionibacterium acnes and Lipopolysaccharide Induced Hepatic Injury in Mice, Chemical and Pharmaceutical Bulletin, 2006, pp. 496-500, vol. 54.
I.-Hung Lee et al., *Antrodia camphorata* Polysaccharides Exhibit Anti-Hepatitis B Virus Effects, FEMS Microbiology Letters, 2002, pp. 63-67, vol. 209.
Masao Hattori, Metabolism and Disposition of Antrodin C (Hepasim) from the Mycelium of *Antrodia cinnamomea* in Rats, The Second Taiwan and Japan Symposium on *Antrodida cinnamomea*, Abst., 2007, pp. 1-9.
Stephen M. Berge et al., Pharmaceutical Salts, Journal of Pharmaceutical Sciences, Jan. 1977, pp. 1-19, vol. 66, No. 1.

* cited by examiner

*Primary Examiner* — Sun Jae Yoo
(74) *Attorney, Agent, or Firm* — WPAT, P.C.; Anthony King; Kay Yang

(57) ABSTRACT

The present invention relates to compounds from mycelium of *Antrodia cinnamomea*. The present invention also relates to a composition and a method for treating or prophylaxis of hepatitis C virus (HCV) infection.

3 Claims, 4 Drawing Sheets

US 8,772,329 B2

COMPOUNDS FROM MYCELIUM OF *ANTRODIA CINNAMOMEA* AND USE THEREOF

FIELD OF THE INVENTION

The present invention relates to compounds from mycelium of *Antrodia cinnamomea*. The present invention also relates to a composition and a method for treating or prophylaxis of hepatitis C virus (HCV) infection. $2^{nh}$

DESCRIPTION OF PRIOR ART

It is estimated that approximate 3% of the world's population is infected with hepatitis C virus (HCV). In developed countries, chronic hepatitis C is the leading cause for cirrhosis, hepatocellular carcinoma, and liver transplantation. The protease of hepatitis C virus is required for the cleavage of viral nonstructural polyprotein to form the mature virus and represents one of the attractive therapeutic targets for developing antiviral agents against HCV (Liu et al., 2004; Hepatitis C NS3 protease inhibition by peptidyl-a-ketoamide inhibitors: kinetic mechanism and structure. *Arch Biochem Biophys* 421: 207-216; Kakiuchi et al., 1999 A high throughput assay of the hepatitis C virus nonstructural protein 3 serine proteinase. *J Virol* 80: 77-84).

The use of herbal therapy and folk medicines has been known for thousands of years in China. In fact, records on the use of herbs date back to biblical times. However, only recently have scientists begun exploring the possible role for herbs in treatment of viral infections. For example, extracts from the root of the Ecballium Elaterium have been used to treat HCV and HBV (EP 0793964 and U.S. Pat. No. 5,648,089). While research in the field of herbal medicines has increased, much remains to be learned about the effectiveness of such herbal remedies.

The fruiting body of *Antrodia cinnamomea* Chang & W N Chou (Basidiomycetes, synonym A. camphorate Wu) is a highly valued folk medicine in Taiwan. It is used as an antidote and for diarrhea, abdominal pain, hypertension, itchy skin, and liver cancer. Some bioactive constituents from the fruiting body of *Antrodia cinnamomea* have been isolated and characterized as a series of polysaccharides, steroids, triterpenoids, and sesquiterpene lactone (Lin et al., 2007, Factors affecting mycelial biomass and exopolysaccharide production in submerged cultivation of *Antrodia cinnamomea* using complex media. *Bioresource Technology* 98: 2511-2517). In previous studies, five new maleic and succinic acid derivatives (antrodin A-E) are isolated from the mycelium of *Antrodia cinnamomea* (Nakamura et al., 2004, Five new maleic and succinic acid derivatives from the mycelium of *Antrodia comphorata* and their cytotoxic effects on LLC tumor cell line. *J Nat Prod* 67: 46-48).

U.S. Pat. No. 7,109,232 discloses compounds 1-5 from *Antrodia cinnamomea* and their use such as hepatoprotection, anti-inflammation or anti-tumor activity and preparation.

SUMMARY OF THE INVENTION

Accordingly, an object of the present invention is to provide novel compounds from mycelium of *Antrodia cinnamomea*.

Another object of the present invention is to provide a pharmaceutical composition for treating or prophylaxis hepatitis C virus infection, comprising a compound of the present invention in an amount effective to attenuate infectivity of said virus, and a pharmaceutically acceptable carrier.

Further object of the present invention is to provide a method for treating or prophylaxis hepatitis C virus infection which comprises administering to a subject in need thereof a pharmaceutically effective amount of a composition comprising the compounds from mycelium of *Antrodia cinnamomea*.

DETAILED DESCRIPTION OF THE INVENTION

Since the mycelium of *Antrodia cinnamomea* was recently reported to be clinically effective for hepatitis patients infected with HCV (Akiba T et al. 2007. Clinical study of Shoshi on Japanese hepatitis patients infected with C type hepatitis virus. *The second Taiwan and Japan Symposium on Antrodia cinnamomea*, Abst. pp. 82-98), a SensoLyte™ 520 HCV protease assay kit was applied to investigate the HCV-protease inhibitory activity of the isolated antrodins, the metabolites of antrodin C as well as one metabolite analogue. The assay method with a quenched-fluorogenic peptide substrate can be used for measure the activity of inhibitors as well as for continuous recording of the progress of the enzyme reaction. Using this assay method, the mode of inhibition of the most potent compound was studied by Lineweaver-Burk plot.

As shown in Table 1, of the 5 constituents (compounds 1-5) from mycelium of *Antrodia cinnamomea*, four of them (compounds 1 and 3-5) showed inhibitory activity on HCV protease. Compounds 6-8, the newly formed in vivo metabolites (or metabolite analogue) of antrodin C showed activity too. Compound 1, which was isolated from *Antrodia cinnamomea* and was also detected in vivo as one of the major metabolite of compound 3, showed the most potent activity with an IC5o less than 1 µg/ml.

Figure 1:
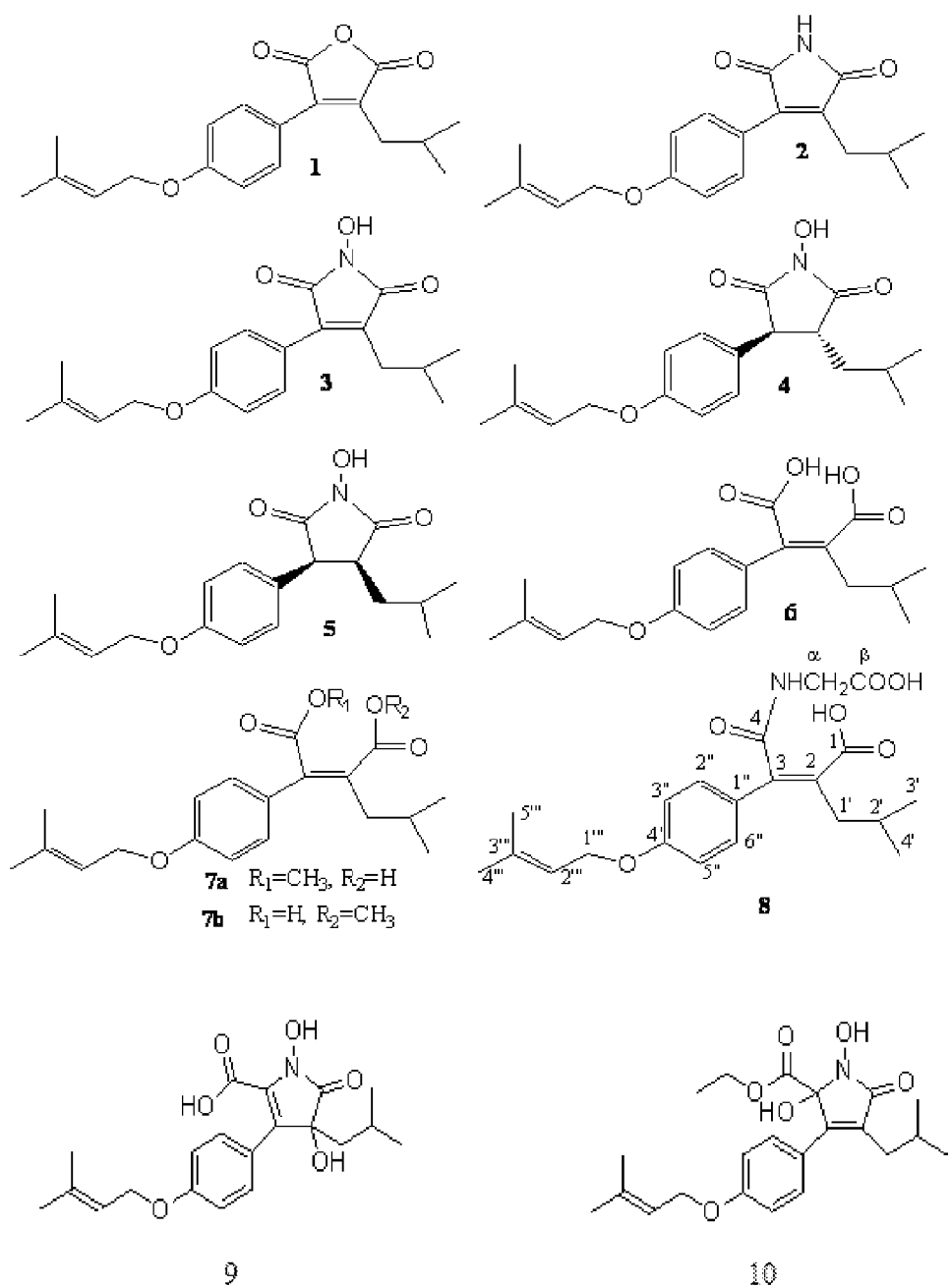
FIG. 1 depicts the structure of the compounds 1-10 from the mycelium of *Antrodia cinnamomea*.
Figure 2:
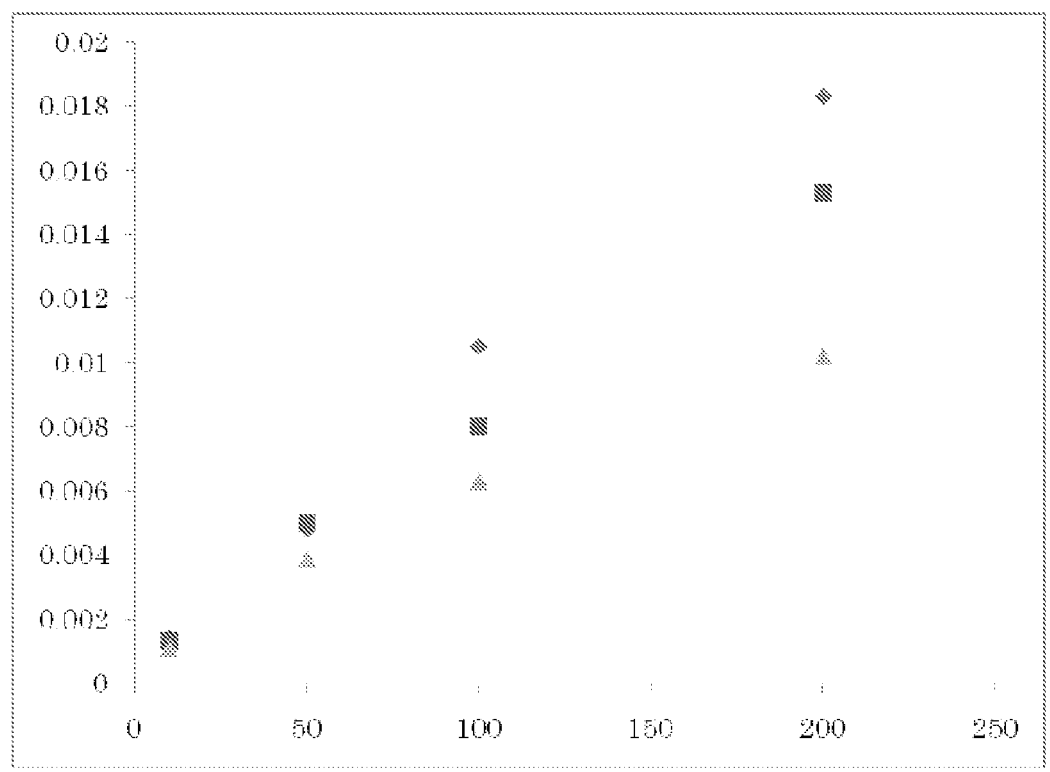
FIG. 2 illustrates Lineweaver-Burk plot (1/Vi v.s. 1/[S]) for the inhibition of HCV-NS3 protease by compound 1 in the presence of various concentrations of substrate (◊:10 µg/ml, □: 5 µg/ml and ○: 0µ).

The mode of inhibition was kinetically analyzed by plotting the enzyme activity at different concentrations of the substrate (10, 50, 100 and 200 times dilution of the substrate stocking solution) with (5 µg/ml, and 10 µg/ml) and without [0 µg/ml (DMSO)] compound 1. As shown in FIG. 2 the mode of HCV PR inhibition by compound 1 was found to be competitive.

Traditionally, the fruit body of *Antrodia cinnamomea* has been used for liver cancer (Lin E S, Chen Y H. 2007. Factors affecting mycelial biomass and exopolysaccharide production in submerged cultivation of *Antrodia cinnamomea* using complex media.

*Bioresource Technology* 98: 2511-2517). Polysaccharides of *Antrodia cinnamomea* has been show to have hepatoprotective effect (Han et al., 2006b, Protective effects of a neutral polysaccharide isolated from the mycelium of *Antrodia cinnamomea* on *Propionibacterium acnes* and lipopolysaccharide induced hepatic injury in mice. *Chem Pharm Bull* 54: 496-500) and anti-hepatitis B virus activity (Lee et. al., 2002, *Antrodia camphorate* polysaccharides exhibit anti-hepatitis B virus effects. *FEMS Microbiol Lett* 209:63-67). Of the maleic and succinic acid derivatives, antrodin C (compound 3) showed protective activity in *Propionicbacterium acnes* and lipopolysaccharide treated mice (Nakamura N, Five new maleic and succinic acid derivatives from the mycelium of *Antrodia comphorata* and their cytotoxic effects on LLC tumor cell line. *J Nat Prod* 67: 46-48). Quantitative analysis showed that compound 3 was the most abundant compound of this chemical type in the mycelium with a content of ca. 5% of the dry weight of mycelia (Han et al., 2006a, Protective effects of a neutral polysaccharide isolated from the mycelium of *Antrodia cinnamomea* on *Propionibacterium acnes* and lipopolysaccharide induced hepatic injury in mice. *Chem Pharm Bull* 54: 496-500). Research on the in vivo metabolism of compound 3 revealed that this compound was converted to six metabolites, i.e. compounds 1, 2, 6, 7a, 7b and an analogue of compound 8. Pharmacokinetic study on compound 3 demonstrated that this compound was quickly absorbed from the gastrointestinal tract followed by rapid and complete metabolization in liver in such a degree that compound 3 itself could not be detected in the body after absorption (Masao Hattori, 2007. Metabolism and Disposition of Antrodin C (Hepasim) from the Mycelium of *Antrodia cinnamomea* in Rats. *The second Taiwan and Japan Symposium on Antrodia cinnamomea*, Abst. pp. 1-9). This pharmacokinetic property as shown in Table 1 suggested that the metabolites are responsible for in vivo pharmacological activities of compound 3 and consequently of the folk medicine. All those metabolites and the constituents of the mycelium of *Antrodia cinnamomea* except for compound 2 showed inhibitory activity on HCV protease. These results strongly support the use of this folk medicine for liver cancer which is often caused by long term infection of hepatitis C virus. The active compounds used in the present invention could be served as leading compounds for the development of potent anti-hepatitis C agents through the mechanism of inhibition against the virus protease.

TABLE 1

IC$_{50}$ values of antrodins and the metabolites against HCV protease.

| Sample | IC$_{50}$ (µg/ml) |
| --- | --- |
| 1[a,b] | 0.9 |
| 2[a,b] | >100 |
| 3[a] | 2.9 |
| 4[a] | 20.0 |
| 5[a] | 20.1 |
| 6[b] | 6.6 |
| 7[b] (7a:7b:1 = ca 5:8:4) | 1.2 |
| 8[c] | 57.5 |
| Embelin | 4.1 |

[a]Constituent of the mycelium of *Antrodia cinnamomea*;
[b]in vivo metabolite of antrodin C;
[c]analogue of one of the in vivo metabolite of antrodin C.

Accordingly, the present invention provides a compound having the formula

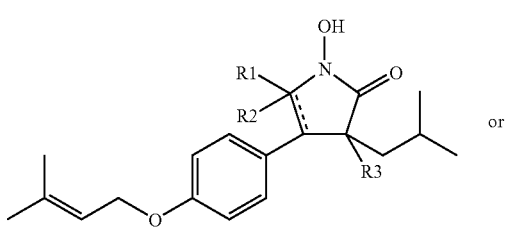 

I

-continued

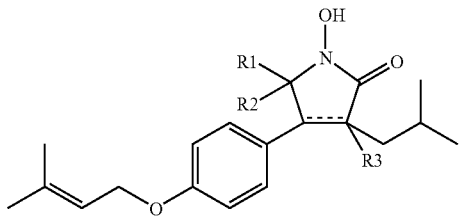

II wherein
═ denotes a single or double bond;
R$_1$ is —(CH$_2$)$_n$COOH or —(CH$_2$)$_n$COOC$_m$H$_{2m+1}$ wherein n is 0-6 and m is 1-6;
R$_2$ is absent, H or OH, and
R$_3$ is absent, H or OH.

In a preferred compound of the present invention, the compound having formula I wherein R$_1$ is COOH; R$_2$ is absent and R$_3$ is OH.

In an alternative preferred compound of the present invention, the compound having formula II wherein R$_1$ is COOCH$_3$, R$_2$ is OH and R$_3$ is absent.

The present invention further provides a compound having the formula III

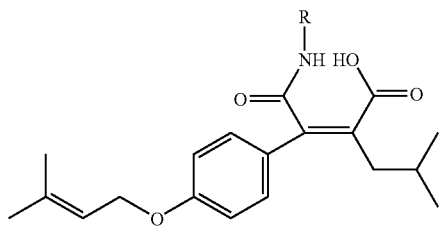

III wherein
R is —(CH$_2$)$_k$COOH or —(CH$_2$)$_k$COO(C$_m$H$_{2m+1}$) wherein k is 0-6 and m is 0-6.

In a preferred compound of formula III, R is —CH$_2$COOH.

Certain compounds exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha.- and beta.-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

Unless otherwise specified, the compounds of the present invention include all such isomeric forms, including (wholly or partially) racemic and other mixtures thereof. Methods for the preparation (e.g. asymmetric synthesis) and separation (e.g. fractional crystallization and chromatographic means) of such isomeric forms are either known in the art or are readily obtained by adapting the methods taught herein, or known methods, in a known manner.

Unless otherwise specified, the compounds of the present invention include also includes ionic, salt, solvate, and protected forms of thereof. It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

The pharmaceutically acceptable salts of the compounds are prepared following procedures which are familiar to those skilled in the art.

The present invention provides a pharmaceutical composition for treating or prophylaxis hepatitis C virus infection, comprising effective amount of a compound having formula I, II or III, and a pharmaceutically acceptable carrier.

The present invention also provides a pharmaceutical composition for treating or prophylaxis hepatitis C virus infection, comprising (i) an effective amount of a compound having formula IV

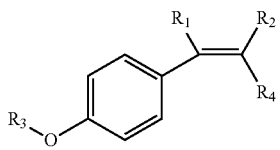

wherein
$R_1$ is $C_{1-10}$ carboxylic acid or $C_{1-10}$ ester;
$R_2$ is $C_{1-10}$ carboxylic acid or $C_{1-10}$ ester;
$R_3$ is H, $C_{1-10}$ alkyl, $C_{2-10}$ alkenyl or $C_{2-10}$ alkynyl; and
$R_4$ is H, $C_{1-10}$ alkyl, $C_{2-10}$ alkenyl or $C_{2-10}$ alkynyl;
or
(ii) a compound having formula V

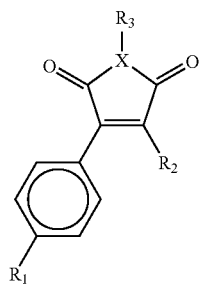

wherein
X is N or O;
$R_1$ is $C_{1-10}$ alkyloxy, $C_{2-10}$ alkenyloxy, or $C_{2-10}$ alkynyloxy;
$R_2$ is H, $C_{1-10}$ alkyl, $C_{2-10}$ alkenyl or $C_{2-10}$ alkynyl; and
$R_3$ is absent, H or hydroxy;
provided that if X is O, $R_3$ is absent; and
a pharmaceutically acceptable carrier.

In the pharmaceutical composition of the present invention, the preferred compound is selected from
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
3R*,4S*-1-hydroxy-3-isobutyl-4-[4-(3-methyl-2-butenyloxy)phenyl]pyrrolidine-2,5-dione,
3R*,4R*-1-hydroxy-3-isobutyl-4-[4-(3-methyl-2-butenyloxy)phenyl]pyrrolidine-2,5-dione.
(2Z)-2-isobutyl-3-{4-[(3-methylbut-2-en-1-yl)oxy]phenyl}but-2-enedioic acid,
(2Z)-2-isobutyl-3-{4-[(3-methylbut-2-en-1-yl)oxy]phenyl}but-2-enedioic acid 4-methyl ester; or
(2Z)-2-isobutyl-3-{4-[(3-methylbut-2-en-1-yl)oxy]phenyl}but-2-enedioic acid 1-methyl ester.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.5% and not more than 90% by weight based on the total weight of the composition, including carrier medium and/or auxiliary agent(s). Preferably, the proportion of active agent varies between 5%-50% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The present invention further provides a method for treating or prophylaxis hepatitis C virus infection which comprises administering to a subject in need thereof a pharmaceutically effective amount of an active agent selected from (1) a compound having the formula

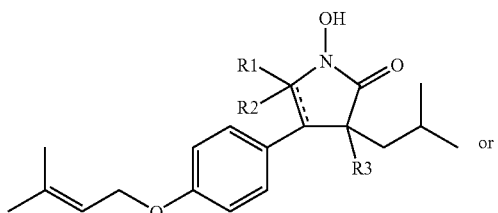

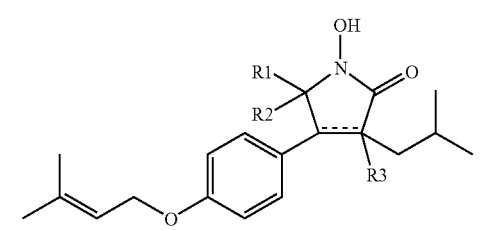

wherein
⎯ denotes a single or double bond;

$R_1$ is —$(CH_2)_n$COOH or —$(CH_2)_n$COO$C_mH_{2m+1}$ wherein n is 0-6 and m is 1-6;
$R_2$ is absent, H or OH, and
$R_3$ is absent, H or OH;

(2) a compound having the formula III

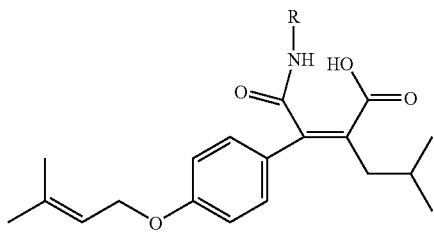

III wherein
R is —$(CH_2)_k$COOH or —$(CH_2)_k$COO$(C_mH_{2m+1})$ wherein k is 0-6 and m is 0-6;

(3) a compound having the formula

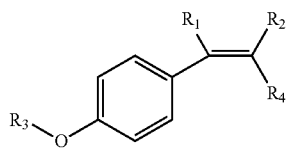

IV wherein
$R_1$ is $C_{1-10}$ carboxylic acid or $C_{1-10}$ ester;
$R_2$ is $C_{1-10}$ carboxylic acid or $C_{1-10}$ ester;
$R_3$ is H, $C_{1-10}$ alkyl, $C_{2-10}$ alkenyl or $C_{2-10}$ alkynyl; and
$R_4$ is H, $C_{1-10}$ alkyl, $C_{2-10}$ alkenyl or $C_{2-10}$ alkynyl;
or (4) a compound having the formula

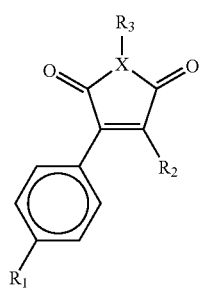

V wherein
X is N or O;
$R_1$ is $C_{1-10}$ alkyloxy, $C_{2-10}$ alkenyloxy, or $C_{2-10}$ alkynyloxy;
$R_2$ is H, $C_{1-10}$ alkyl, $C_{2-10}$ alkenyl or $C_{2-10}$ alkynyl; and
$R_3$ is absent, H or hydroxy;
provided that if X is O, $R_3$ is absent.

In a preferred embodiment of the present invention, active agent is selected from

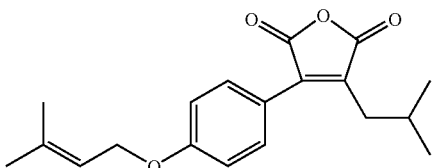
1

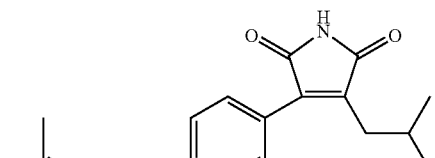
2

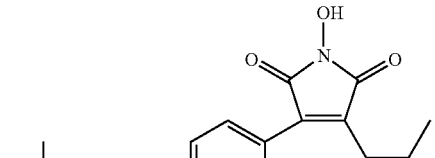
3

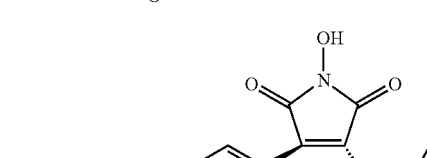
4

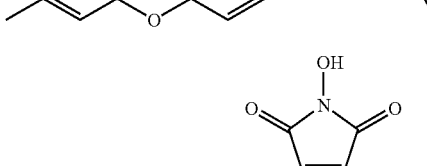
5

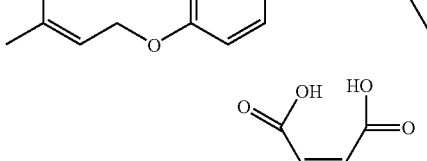
6

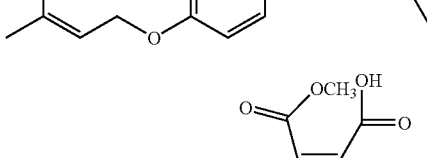
7a

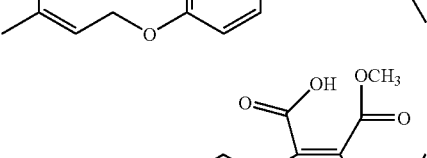
7b

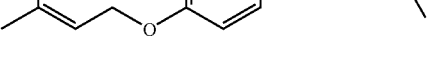

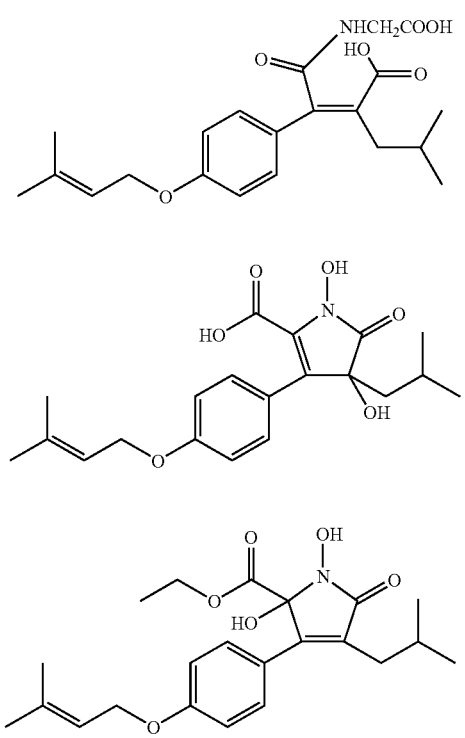

The compounds of the invention may be administered using any amount and any route of administration effective for attenuating infectivity of the hepatitis C virus. Thus, the term "effective amount" used herein refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like. The anti-hepatitis C compounds are preferably formulated in dosage unit form for ease of administration and uniformity of dosage. Dosage unit form as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium.

The compounds of the invention may be administered orally, parenterally, such as by intramuscular injection, intraperitoneal injection, intravenous infusion or the like, depending on the severity of the infection being treated.

Although the compounds of the present invention can be administered to any patient which is susceptible to hepatitis C infection, the compounds are intended for the treatment of mammalian hosts, and especially humans.

In view of the inhibitory effect on enzyme activity produced by the compounds of the invention, it is anticipated that these compounds will be useful not only for therapeutic treatment of infection, but for hepatitis C viral prophylaxis, as well. The above-noted dosages will be essentially the same whether for treatment or prophylaxis of hepatitis C infection.

The term "organic solvent" used herein includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human. Especially, the compounds 9 and 10 are prepared from organic solvent extract from *Antrodia cinnamomea*.

The following examples are provided to describe the invention in further detail. These examples, which set forth the best mode presently contemplated for carrying out the invention, are intended to illustrate and not to limit the invention.

EXAMPLE

The examples below are non-limiting and are merely representative of various aspects and features of the present invention.

Apparatus.

NMR spectra were obtained on a Varian Unity Plus 500 ($^1$H, 500 MHz; $^{13}$C, 125 MHz) spectrometer. MS spectrum was measured on an electrospray ionization mass spectrometer (ESI-MS, Esquire 3000$^{Plus}$, Bruker Daltonik GmbH, Bremen, Germany).

Materials for HCV Protease Assay.

HCV NS3/4A protease (lot# Lot 046-047 for the screening and lot# Lot 046-079 for the mechanism study) and SensoLyte™ 520 HCV Protease Assay Kit *Fluorimetric* (lot# AK 71147-1005) were purchased from AnaSpec, San Jose, Calif., USA. The substrate was a 5-FAM/QXL™520 FRET peptide based on the sequence of Ac-Asp-Glu-Asp(EDANS)-Glu-Glu-Abu-Ψ-[COO]Ala-Ser-Lys(DABCYL)-NH2. The assay was carried out on BD Falcon™ Microtest™384-well 120 μl black assay plates (lot#05391155). Fluorescence was measured by TECAN GENios plate reader at excitation/emission 485/530 nm Chemical compounds. Antrodins A-E (compounds 1-5) were isolated from the mycelium of *Antrodia cinnamomea* as reported (Nakamura et al., 2004. Five new maleic and succinic acid derivatives from the mycelium of *Antrodia comphorata* and their cytotoxic effects on LLC tumor cell line. *J Nat Prod* 67: 46-48). Embelin used as a positive control was isolated in our laboratory in previous work (Hussein et al., 2000, Inhibitory effects of Sudanese medicinal plant extracts on hepatitis C virus (HCV) Protease. *Phytother Res* 14: 510-516). Compounds 6, 7a and 7b were detected as the metabolites of antrodin C in vivo. Compounds 7a and 7b were un-separable due to the equilibrium of these two compounds through compound 1. It was thus used for the assay as a mixture of compounds 1, 7a and 7b and named 7. Compound 8 was an analogue of another metabolite whose glycine group was supposed to connect to the other carboxyl group in the structure.

Example 1

Synthesis of Compound 8

A pyridine (5 mL) solution of 1 (314 mg, 1 mmol), 4-(dimethylamino)pyridine (122 mg, 1 mmol) and glycine (113 mg, 1.5 mmol) was heated at 40° C. for 12 h and then kept at room temperature overnight. The product mixture was partitioned between EtOAc and 0.2N HCl solution. The EtOAc layer was washed with water and concentrated to dryness. The residue was chromatographed over ODS eluted with $CH_3CN$—$H_2O$ (30-100%) to obtain compound 8 from the 60% $CH_3CN$ eluted part (200 mg, 51%). $^1H$ NMR (DMSO-$d_6$, 500 MHz): δ 0.81, 0.82 (3H each, s, H-3', 4'), 1.71, 1.75 (3H each; s, H-4''', 5'''), 1.93 (1H, m, H-2'), 2.50 (overlapped with NMR solvent, H-1'), 4.20 (2H, s, H-a), 4.58 (2H, d. ˆ=6.5 Hz, H-1'''), 5.45 (1H, m, H-2'''), 7.07 (2H, d, J=9.0 Hz, H-3'', 5''), 7.52 (2H, d, J=9.0 Hz, H-2'', 6''). $^{13}C$ NMR (DMSO-$d_6$, 125 MHz): δ 18.1 (5'''), 22.5 (3', 4'), 25.8 (4'''), 27.5 (2'), 32.2 (1'), 39.5 (a), 64.5 (1'''), 114.9 (3'', 5''), 119.6 (2''), 120.9 (1''), 130.9 (2'', 6''), 137.4 (3), 137.6 (3'''), 137.9 (2), 159.5 (4''), 169.1 (4), 170.4 (β), 171.1 (1). ESI-MS (negative): ink 370.0 ([M-$H_2O$-H]-, 100%).

Assay Procedure:

Compound 6 was dissolved in $H_2O$ and other compounds were dissolved in DMSO for the assay. To each well were added 2 μl of respective compound solution and 8 μl of freshly diluted enzyme (0.5 μg/ml). The reaction was started by adding 10 μl of freshly diluted substrate (100 times dilution of a DMSO stocking solution). After being incubated at room temperature (28° C.) for 30 min, the fluorescence intensities were measured at Ex/Em=485 nm/535 nm. Inhibition percentages were calculated as $100 \times (F_{vehicle} - F_{sample})/F_{vehicle}$ =% inhibition, where F is the fluorescence value of vehicle control or of compound minus the fluorescence of the substrate control.

Example 2

Synthesis of Compounds 9 and 10

*Antrodia camphorata* mycelia powder (ACM) (200 g), from Simpson Biotech Co. Ltd., Taiwan, were four times extracted with hot EtOH (4 l) per each. After removal of residues by filtration, the EtOH extract was transferred to separatory funnels. Water and $CH_2Cl_2$ (1:1) were added and was mixed for approximately 1-5 minutes. The addition and mixing were repeated by four times. The aqueous was separated and the $CH_2Cl_2$ layer was subjected to Diaion HP20 column chromatography, and then eluted with from 70%, 80%, 90% to 100% MeOH to give fourteen fractions (Fr. 1-14). Fraction 3 was chromatographed on OPN-75 Packing Column (resin, Merck) and eluted with MeOH to give three fractions (Fr. 15-17). Fraction 16 was chromatographed on Sephadex LH20 column and eluted with 100% MeOH to give six fractions (Fr. 18-23). Fraction 20 was separated by preparative HPLC [column: Cosmosil 5C18-AR-II (20×250 mm)] to give compound 9.

TABLE 1

$^1$H-NMR Spectral Data of Compound 9

| | | | | |
|---|---|---|---|---|
| 2 | 166.2 (s) | | 2.07; 2.35 (weak) | 2 |
| 3 | 88.4 (s) | | 1.67; 2.07; 2.35 | 11 |
| 4 | 131.8 (s) | | 2.07 (weak); 2.35; 8.01 | 5 |
| 5 | 135.6 (s) | | | 6 |
| 1' | 43.9 (t) | 2.07 (1H, m); 2.35 (1H, m) | 0.82; 0.84; 1.67 | 13 |
| 2' | 24.1 (d) | 1.67 (1H, m) | 0.82; 0.84; 2.07; 2.35 | 16 |
| 3' | 24.1 (q) | 0.82 (3H, d, 6.5 Hz) | 0.84; 1.67; 2.07; 2.35 | 15 |
| 4' | 23.5.5 (q) | 0.84 (3H, d, 6.5 Hz) | 0.82; 1.67 | 17 |
| 1'' | 121 (s) | | 6.92 | 8 |
| 2'', 6'' | 130.9 (d) | 8.01 (2H, d, 9.0 Hz) | 8.01 | 7 |
| 3'', 5'' | 114.6 (d) | 6.92 (2H, d, 9.0 Hz) | 6.92 | 10 |
| 4'' | 159.7 (s) | | 4.51; 6.92; 8.01 | 3 |
| 1''' | 64.8 (t) | 4.51 (2H, d, 7.0 Hz) | | 12 |
| 2''' | 119.2 (d) | 5.46 (1H, bro, 6.5 Hz) | 1.72; 1.78; 4.51 | 9 |
| 3''' | 138.7 (s) | | 1.72; 1.78; 4.51 | 4 |
| 4''' | 25.8 (q) | 1.78 (3H, s) | 1.72 | 14 |
| 5''' | 18.2 (q) | 1.72 (3H, s) | 1.78; 5.46 | 18 |
| —COOCH$_2$ | 168.9 (s) | | | 1 |

Fraction 21 was subsequently separated by preparative HPLC [column: Cosmosil 5C18-AR-II (20×250 mm)] to give compound 10.

TABLE 2

$^1$H-NMR Spectral Data of Compound 10

| | | | | |
|---|---|---|---|---|
| 2 | 172.1 (s) | | 2.33 | 1 |
| 3 | 133.7 (s) | | 2.00; 2.33 | 6 |
| 4 | 148.5 (s) | | 2.33; 7.22 | 4 |
| 5 | 90.4 (s) | | | 11 |
| 1' | 33.1 (t) | 2.33 (2H, d, 1.5; 7.0 Hz) | 0.79; 0.81; 2.00 | 14 |
| 2' | 27.2 (d) | 2.00 (1H, m) | 0.79; 0.81; 2.33 | 15 |
| 3' | 22.5 (q) | 0.81 (3H, d, 6.5 Hz) | 0.79; 2.00; 2.33 | 17 |
| 4' | 22.3 (q) | 0.79 (3H, d, 6.5 Hz) | 0.81; 2.00; 2.33 | 18 |
| 1'' | 123.1 (s) | | 6.89 | 8 |
| 2'', 6'' | 129.9 (d) | 7.22 (2H, d, 8.5 Hz) | 7.22 | 7 |
| 3'', 5'' | 114.8 (d) | 6.89 (2H, d, 8.5 Hz) | 6.89 | 10 |
| 4'' | 159.6 (s) | | 4.50; 6.89; 7.22 | 3 |
| 1''' | 64.79 (t) | 4.50 (2H, d, 6.5 Hz) | | 12 |
| 2''' | 119.2 (d) | 5.46 (1H, tt,, 1.5; 5.5 Hz) | 1.72; 1.78; 4.50 | 9 |
| 3''' | 138.7 (s) | | 1.72; 1.78; 4.50 | 5 |
| 4''' | 25.8 (q) | 1.78 (3H, s) | 1.72; 5.46 | 16 |
| 5''' | 18.2 (q) | 1.72 (3H, s) | 1.78; 5.46 | 19 |
| —COOCH$_2$ | 169.2 (s) | | 4.29 | 2 |
| —OCH$_2$CH$_3$ | 64.0 (t) | 4.29 (2H, m) | 1.22 | 13 |
| —OCH$_2$CH$_3$ | 14.0 (q) | 1.22 (3H, t, 7.5 Hz) | 4.29 | 20 |

Sample Treating Before HPLC
1. Powder 0.2217 g mycelium of *Antrodia cinnamomea* in 5 mL alcohol.
2. After 30 minutes for extraction of ultrasonic vibration, centrifuge it in 9500 rpm for 5 minutes, then supernatant liquid filter through 0.45 μm screen filter.
3. HPLC analyze sample.

Figure 3:
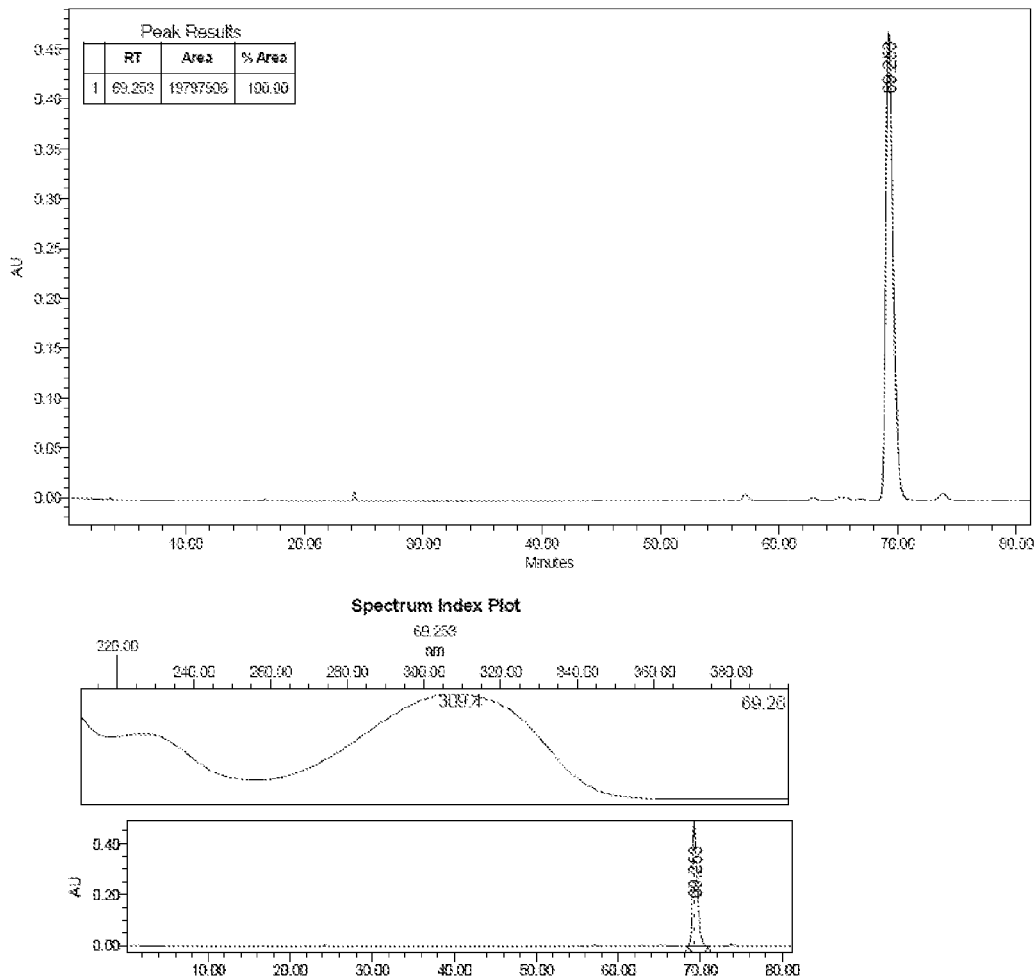
FIG. 3 is analytic data of compound 9 of the present invention.
Figure 4:
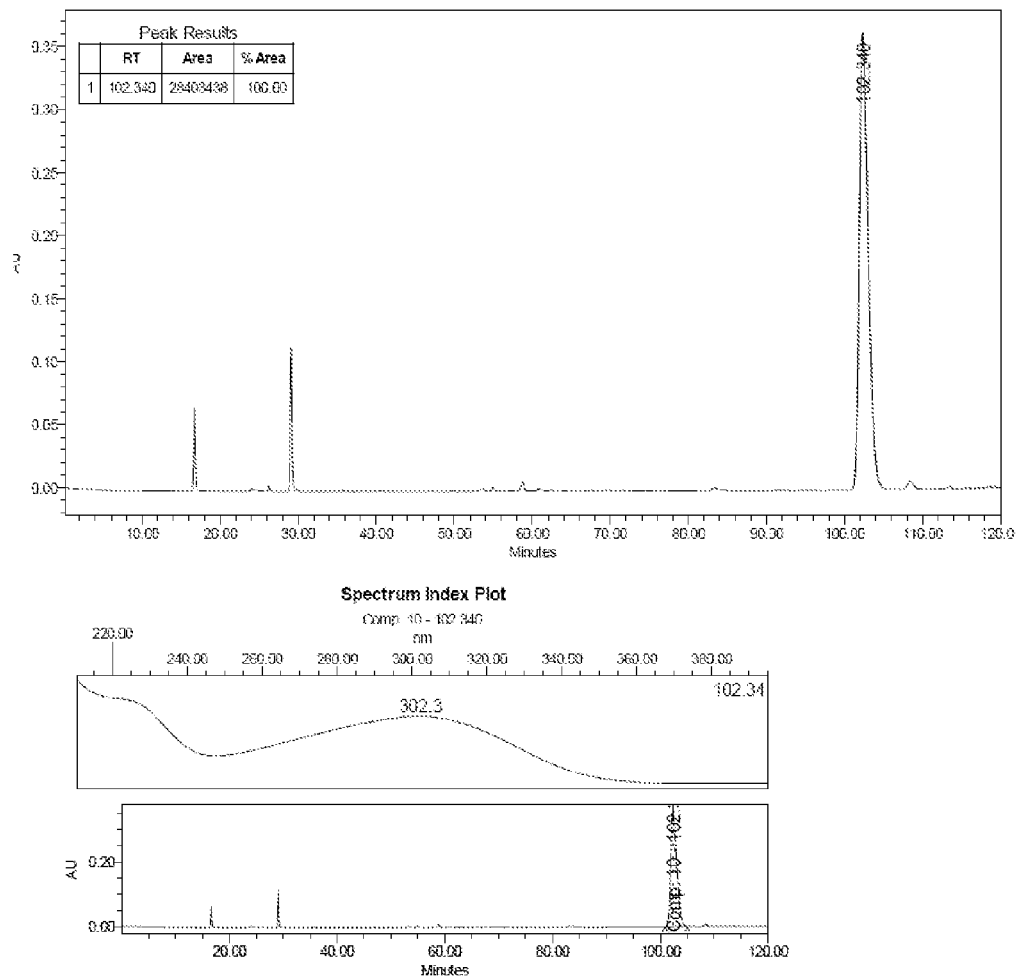
FIG. 4 is analytic data of compound 10 of the present invention.

HPLC Assay Condition:
1. Mobile phase: 0.1% $H_3PO_4$, $CH_3CN$, MeOH
2. Column: Agilent, Zorbax SB-C18, 4.6×250 mm
3. Rate: 1 mL/min
4. Wavelength: 254 nm 5. Temperature: 30° C.
6. Injection: 20 μL HPLC Assay Result: (HPLC Analyzing Spectrum in FIGS. 3 & 4)

| Sample | | Retention Time | Area | Concentration in ACM |
|---|---|---|---|---|
| | Compound 9 | 69.253 | 19797906 | — |
| | Compound 10 | 102.34 | 28403438 | — |
| Simpson ACM | Compound 9 | — | — | 2.3 mg/g |
| | Compound 10 | — | — | 0.15 mg/g |

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An isolated compound having the formula III

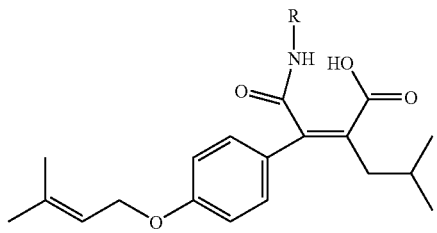

wherein
R is $-(CH_2)_k COOH$ or $-(CH_2)_k COO(C_m H_{2m+1})$
wherein k is 0-6 and m is 0-6.

2. The isolated compound of claim 1, wherein R is $-CH_2COOH$.

3. A pharmaceutical composition for inhibiting hepatitis C virus protease, comprising effective amount of an isolated compound having the formula III

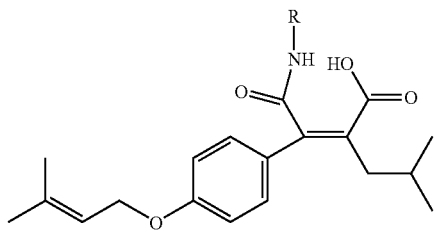

wherein
R is $-(CH_2)_k COOH$ or $-(CH_2)_k COO(C_m H_{2m+1})$
wherein k is 0-6 and m is 0-6,
and a pharmaceutically acceptable carrier.

* * * * *